(12) United States Patent
Coats

(10) Patent No.: US 9,874,505 B2
(45) Date of Patent: *Jan. 23, 2018

(54) VERIFICATION OF GARMENT PROPERTIES USING MULTIPLE TEST COUPONS

(71) Applicant: Phalanx Defense Systems, LLC, Gainesville, FL (US)

(72) Inventor: James Coats, Gainesville, FL (US)

(73) Assignee: PHALANX DEFENSE SYSTEMS, LLC, Gainseville, FL (US)

( * ) Notice: Subject to any disclaimer, the term of this patent is extended or adjusted under 35 U.S.C. 154(b) by 145 days.

This patent is subject to a terminal disclaimer.

(21) Appl. No.: 14/990,848

(22) Filed: Jan. 8, 2016

(65) Prior Publication Data

US 2016/0187103 A1    Jun. 30, 2016

Related U.S. Application Data

(63) Continuation-in-part of application No. 14/770,129, filed as application No. PCT/US2015/032208 on May 22, 2015, now Pat. No. 9,797,689.

(60) Provisional application No. 62/031,228, filed on Jul. 31, 2014.

(51) Int. Cl.
| | |
|---|---|
| G01N 3/313 | (2006.01) |
| G01N 3/30 | (2006.01) |
| F41H 1/02 | (2006.01) |
| A41D 27/20 | (2006.01) |

(52) U.S. Cl.
CPC ............ *G01N 3/313* (2013.01); *F41H 1/02* (2013.01); *G01N 3/30* (2013.01); *A41D 27/204* (2013.01)

(58) Field of Classification Search
CPC . F41H 1/02; G01N 3/30; G01N 3/313; A41D 27/204
See application file for complete search history.

(56) References Cited

U.S. PATENT DOCUMENTS

| | | | | | |
|---|---|---|---|---|---|
| 6,108,816 | A | * | 8/2000 | Bradley | A62B 99/00 182/3 |
| 6,115,948 | A | * | 9/2000 | Mitchell | A41D 27/08 2/245 |
| 6,233,747 | B1 | * | 5/2001 | Barker | A41D 27/20 2/247 |
| 2003/0221244 | A1 | * | 12/2003 | Liddell | A41D 27/08 2/244 |
| 2011/0047669 | A1 | * | 3/2011 | Carr | A41D 27/08 2/122 |

* cited by examiner

*Primary Examiner* — Daniel J Colilla
(74) *Attorney, Agent, or Firm* — Sven W. Hanson

(57) ABSTRACT

Multiple test coupons are incorporated in the construction of a personal garment for the purpose of determining the presence of foreign substances acquired during garment use or a change in properties or other change in characteristics over time. Each of the test coupons is retained with the garment during the useful life of the garment until the coupon is individually removed for test purposes. Each test coupon has a construction identical to the garment construction and is easily removable and configured to allow for destructive testing. Sufficient multiple coupons are provided with each garment over its life to allow for periodic testing.

4 Claims, 5 Drawing Sheets

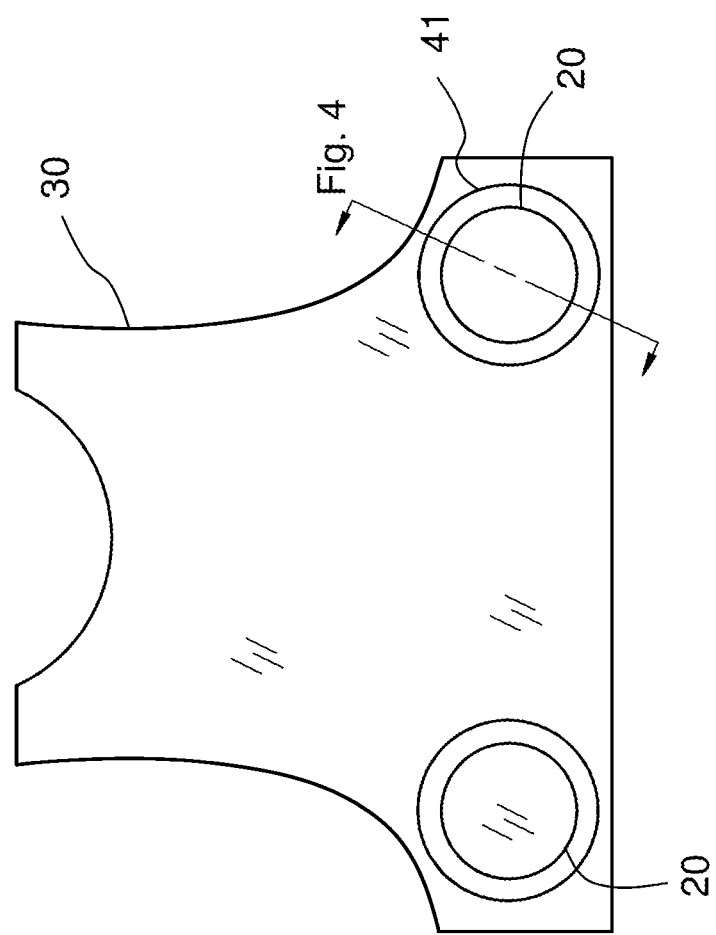

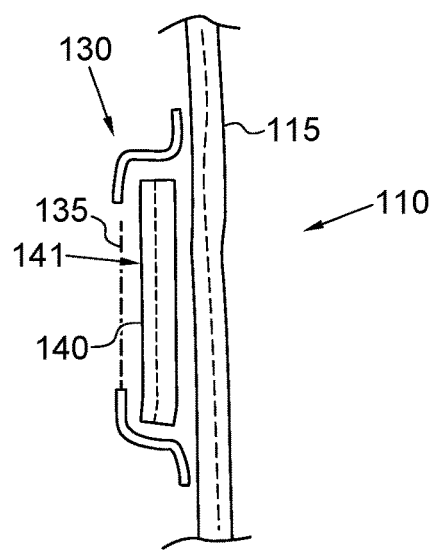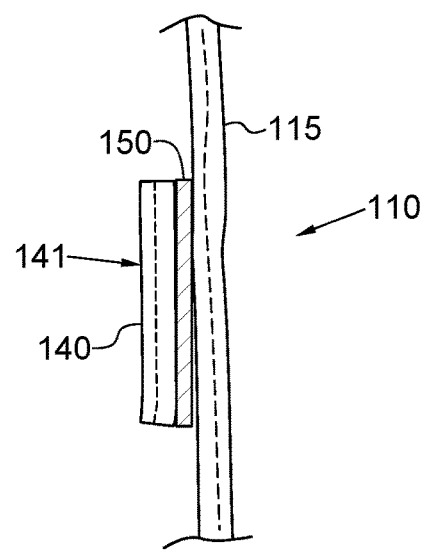
Figure 7A                     Figure 7B

VERIFICATION OF GARMENT PROPERTIES USING MULTIPLE TEST COUPONS

BACKGROUND OF THE INVENTION

The present invention pertains to garments that incorporate devices and mechanisms for determining changes with time of garment properties including construction materials properties and presence of acquired external substances. Specific applications regard testing for the presence of toxic and otherwise deleterious chemicals acquired through use of a garment.

U.S. patent application Ser. No. 14/770,129 to Coats (Coats) discloses incorporating multiple test coupons in the construction of a personal ballistic protection device. Each of the test coupons is retained with the protection device during its use until each coupon is removed for test purposes. Each test coupon has a construction identical to the protective portions of the protective device and is easily removable and configured to allow for destructive testing. Sufficient coupons are provided with the ballistic protection device to allow for periodic testing over a predetermined useful life of the ballistic protection device. The ballistic protection device may be a garment such as a vest. The present patent claims priority from the copending patent application of Coats and applies the same novel concepts to other applications and uses.

The Coats invention particularly addresses garment construction materials and material properties in the context of devices and garments used for protection from ballistic weapons. However, the underlying principles and methods are equally useful in the context of other environmental exposure and time-dependent properties and characteristics of garments.

It has been established that fire emergency workers including firefighters and emergency rescue workers and hazardous materials response workers may have an increased insistence of cancer and other health problems as a result of exposure to fire event related environmental toxic chemicals. Potential known carcinogens posing exposure risks to fire emergency workers include polycyclic aromatic hydrocarbons, asbestos and formaldehyde.

It is also believed that garments worn by fire emergency workers and other personal that work in environments containing toxic and otherwise harmful air-borne chemicals may absorb these chemicals through natural incidental exposure. A worker's exposure time to these chemicals may be substantially increased by a worker's time of exposure to their own garments. Exposure times may be many times that of the fire events duration.

Because, in this context, chemical content testing of garments by conventional means requires destruction of the garments, testing is often not carried out in a useful manner. Due to the high cost of fire emergency garments, such as so called "turnout" gear, and the high cost of cleaning such garments resulting in inadequate cleaning, workers are often at a high risk of exposure from contaminated garments. What is needed is a method of carrying out chemical testing of garments without destruction of the garment.

SUMMARY OF THE INVENTION

The invention is a device and system that incorporates multiple test coupons in the construction of a personal garment for the purpose of determining the presence of foreign substances acquired during garment use or a change in properties or other change in garment construction material characteristics over time. Each of the test coupons is retained with the garment during the useful life of the garment until the coupon is individually removed for test purposes. The coupons are retained in a manner and with a configuration that exposes them to a representative environment. Each test coupon has a construction identical to the garment construction and is easily removable and configured to allow for destructive testing. Sufficient multiple coupons are provided with each garment over its life to allow for periodic testing.

The garment of the invention may take any of many alternative forms and the construction or form of the garment is not limiting. In example applications, the invention includes, alternatively, a ballistic protection vest and a fire-resistant turnout gear, each incorporating multiple test coupons and individual coupon retaining devices.

The inventive system and methods may be applied to identify critical garment construction material properties, or the presence of deleterious materials, that potentially change with time and use. This may include the existence of foreign substances or chemicals not inherently found in garments, but are incidentally or otherwise deposited on or adsorbed by the construction materials of the garment during the intended use of the garment.

The invention includes methods of maintaining or verifying critical properties of garments through periodic destructive testing of coupons. In one example, test coupons have a construction identical to a ballistic resistant shield incorporated in a personal vest. Individual coupons are removed over the life of the vest to be tested to verify the ballistic resistance performance of the vest shield construction.

In other examples of the invention, multiple coupons are retained on a garment designed to be worn by fire-fighting personnel in fire event situations. Individual coupons are removed periodically over the life of the garment and tested for the presence of suspected cancer-causing chemicals. Continued use, or removal from use, may be predicated on results of such tests.

In methods according to the invention, it is preferred to establish a desired useful life period for the garment as a guide determining coupon testing periods. Knowledge of risk factors including potential substance exposure rates, rates of absorption, maximum limits for concentrations or content of substances on the subject garment can be the basis for determining the frequency and number of coupon testing needed. The garment construction with coupons, and the associated testing of coupons, can be effective for determining the presence of suspected substances without predetermination of useful life period. However, application of these constructions and methods to ensure limiting garment user exposures requires predetermination of the appropriate number of coupons and timing of testing.

The invention may take the form of various different embodiments and other aspects of the invention are discussed in the following description of example embodiments.

DESCRIPTION OF THE DRAWINGS

FIG. 3 is a plan view of a ballistic insert incorporated in the construction of the embodiment of FIG. 1.

FIG. 7A is a cross-section view of a test coupon retained in a garment pocket according to the invention.

FIG. 7B is a cross-section view of a test coupon retained on the outer surface of a garment according to the invention.

DETAILS OF EMBODIMENTS OF THE INVENTION

The inventive concept of retaining multiple test coupons on a personal garment, and periodically submitting individuals of the coupons to destructive testing may be applied to garments having different property, characteristic or performance requirements. In the prior patent application by the present inventor (U.S. application Ser. No. 14/770,129, the specification of which is substantially reproduced below) the concept is applied to garments including constructions having ballistic weapon protection properties. Testing of the garment materials is valuable to ensure the desired performance is maintained over an extended lifetime of use. In other applications, subject garments may have other critical properties, material characteristics or performance factors, beneficial or deleterious, that are susceptible to change over time and therefore warrant periodic testing.

In some applications, the subject garment construction or materials may have beneficial properties such as temperature or fire resistance that are susceptible to deterioration due to exposure conditions in use or simply due to time-dependent degradation. In these cases, periodic testing, in the inventive applications, of test coupons retained on the subject garment allow verification of the beneficial properties over the life of the garment without harm to the useful construction of the garment.

In other applications, the subject garment construction or material may potentially acquire deleterious substances, chemicals or properties and testing through the inventive methods is valuable to verify that the substances, chemicals or properties are not present or do not exceed known limits. For example, turnout gear worn by fire fighting personnel is known to acquire cancer causing chemicals in the course of intended use during fire events. Appropriate periodic testing of test coupons retained on (and then removed for testing) the turnout gear, in the manner of the invention, provides a test for the presence of such chemicals on the turnout gear.

FIGS. 1, 2, 3 and 4 illustrate a configuration of a garment including test coupons configured for periodic testing for ballistic resistant properties. The configuration of the test coupons and the manner of retention on the garment is particular to the properties of interest.

Figure 1:
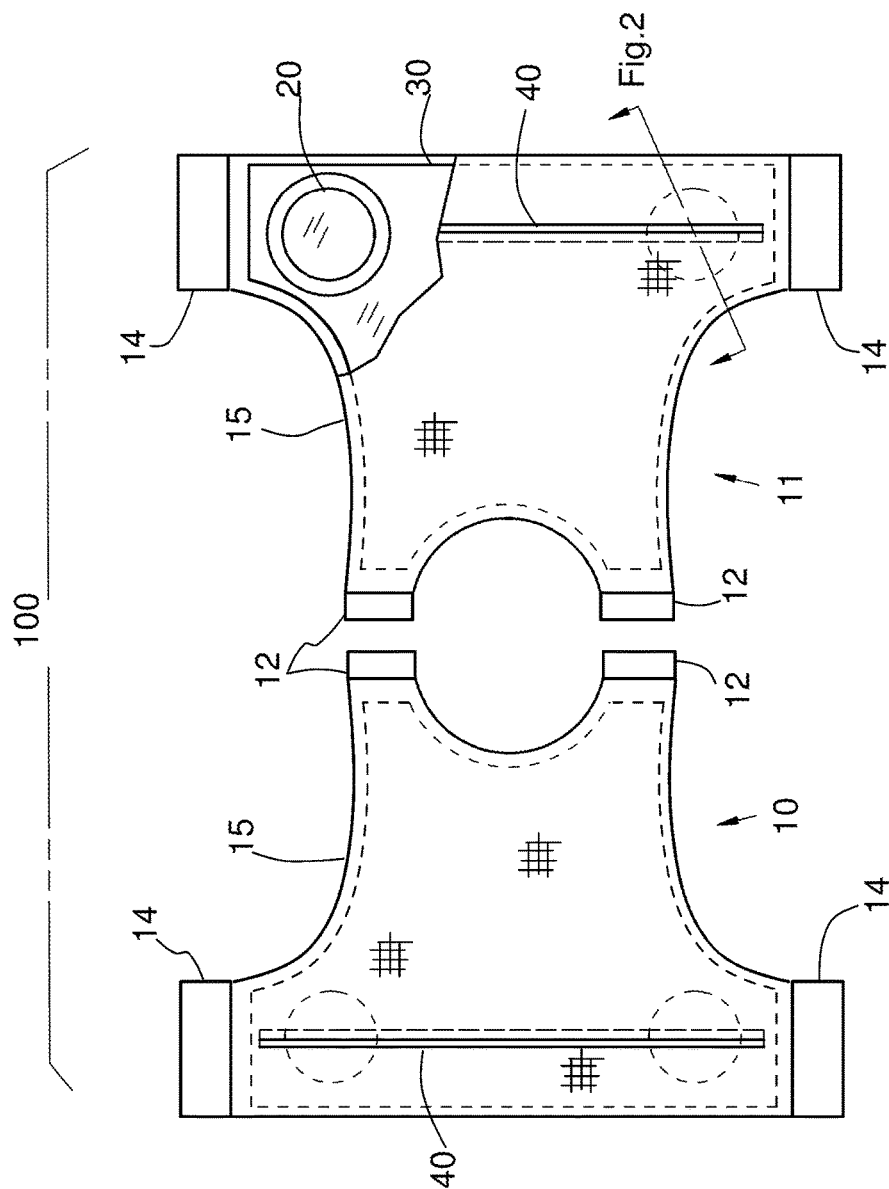
FIG. 1 is plan view of one embodiment of a personal ballistic protection vest according to the invention.
Figure 2:
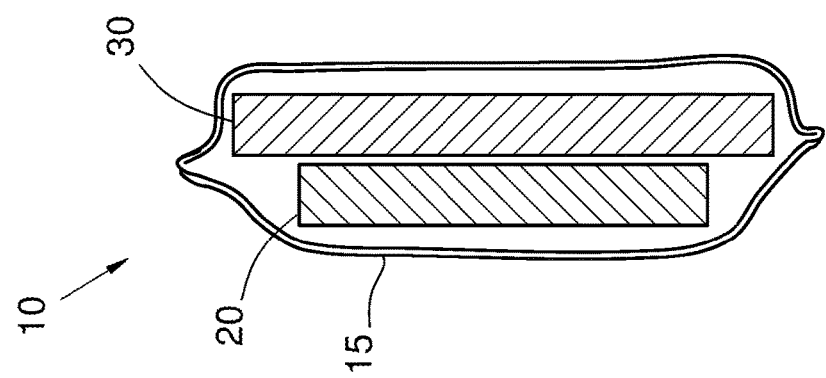
FIG. 2 is a detailed section view on one portion of the construction of FIG. 1.

FIG. 1 is a plan view of a preferred embodiment of the invention in the form of a body armor vest 100 configured to be worn on the upper torso in the manner of a conventional vest garment. The vest includes two separable garment portions 10, 11. They are separable for improved ease of manufacture, assembly and use. FIG. 2 is a section view of one portion (details of the elements in FIG. 2 are discussed below in regard to FIG. 4). The two portions 10, 11 are configured to be joined to form, respectively, the anterior and posterior elements of the vest when worn by a human user.

Each of the two portions 10, 11 are preferably functionally identical and differ only in the nature of their respective mating connecting elements. However, they need not be identical in shape and size and may be altered in these aspects for convenience or alternation of positioning on the user.

Each of the portions 10, 11 includes an outer covering 15 that serves as the main garment element and provides general covering of the user, support for the ballistically functional elements and interconnectivity. For these purposes the covering 15 may be any of a variety of conventional durable flexible fabrics used in the prior art for garmets or safety vests or protection garments, or materials with similar properties.

The portions 10, 11 and respective coverings 15 should include respective shoulder sections configured to cojoin using first fastening elements 12. These fastening elements 12 may be formed of industrial grade "hook and loop" elements, or other devices providing similar function. The portions 10, 11 and respective coverings 15 also include waist sections configured to cojoin using second fastening elements 14 having similar properties and function as the first fastening elements 12. In this way the two portions 10, 11 maybe each assembled as a generally planar element and then the two cojoined on the user to form a body-enclosing barrier for the upper torso.

Each portion 10, 11 includes a ballistic shield 30 that is enclosed within the respective covering 15. The shield 30 is shown in more detail in FIG. 3; this construction is common for the shields in each of the portions 10, 11 in the embodiment illustrated. However, distinct shaped shields may be used where the portions 10, 11 have different shapes. The particular preferred construction of the ballistic shield 30 is detailed below, but generally is configured to provide a specific level of resistance against incident ballistic projectiles for the user while the vest is worn as intended. The overall shape of the shield 30 generally should be maximally extentive over the area of the portions 10, 11 to provide a maximum of ballistic protection to the user. The critical user body areas for protection are known and defined in the prior art. Preferably, in all cases, each portion 10, 11 and shield 30 is shaped and configured to overall a substantial body portion of the intended user's body.

As a convenience, the cover 15 of each portion 10, 11 may include a sealable overlapping opening slit 40 sized and configured to allow passage of the respective shield 30 into and out of the portion 10, 11 both for initial assembly and for removal of test coupons (described below). The slit 40 may have any of a variety of configurations and may be sealed by any of a number of convention devices or methods.

A section of the covering 15 is cut away in FIG. 1 to illustrate the shield 30 and one of four test coupons 20. Each shield 30 includes two coupons in the general manner shown in FIG. 3. Preferably each test coupon 20 is located generally in waist sections for a variety of purposes, including comfort.

Figure 4:
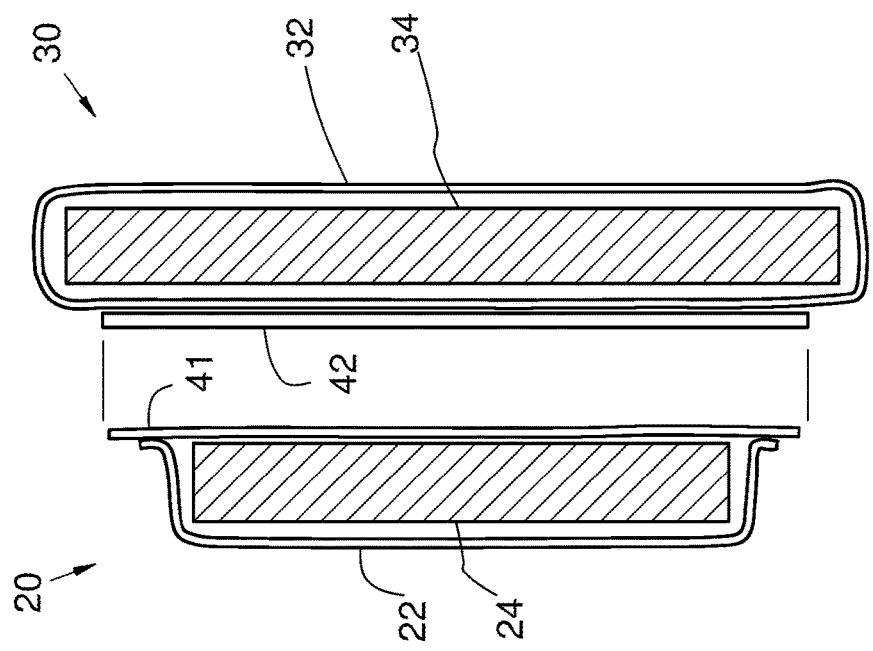
FIG. 4 is a detailed section view of one portion of the device of FIG. 3.

FIG. 4 is a section view of a shield 30 including a test coupon 20. In FIG. 4, the test coupon 20 is separated from the shield 30 for illustration purposes, but it should be clear that each test coupon 20 is physically connected to it's respective shield 30.

Referring particularly to FIG. 4, each shield 30 includes a shield body 34 that provides the ballistic properties required and a flexible wrap 32. The wrap 32 is formed of a flexible material selected to provide an environmental barrier and protection to the shield body 34. For those purposes the wrap may have any of various different properties depending on the constituent materials of the shield body 34. The wrap also provides a convenient handling covering for the shield. Alternatively, the wrap 32 may be an integral element of the shield body 34.

Each test coupon 20 includes a coupon body 24 having a construction identical to that of the shield body 34. Preferably, the coupon body 24 is cut from the same material stock as the shield body 34. Each test coupon 20 preferably includes a coupon covering 22 as a protective element and convenience for handling the coupon body 24. For each test coupon 20, a securing device is provided for securing the test coupon against the shield 30 in the desire location. In the embodiment shown, the securing device is provided by mating "hook and loop" fabric portions 41, 42 attached or integrated into, the test coupon 20 and shield 30. The securing device may take other forms of devices and methods with a common critical function of allowing easy removal of the test coupon 20 after use.

Preferably at least four test coupons 20 are provided with each set of portions 10, 11 forming a vest. The purpose for this configuration is to enable useful destructive testing of coupons over the useful life of the vest. It is known that a four to five year use life is conventional in police and military applications.

In use, approximately one year after a vest as specified here is put into intended use, one test coupon 20 is removed from the vest. The test coupon 20 may then be subjected to any selected testing processes, including destructive testing. Preferably, the test coupon is subjected to a function test of firing a ballistic weapon at the test coupon 20 in a manner functionally simulating the intended use of the vest for user personal protection. This process may be repeated every year for an additional three years. If the selected test criterion is met, the vest may then be continued in use for an additional time, providing a tested useful life of greater than four years. Because removal of the test coupon 20 does not regard the shield 30 itself, testing may be carried out without reducing the useful like of the article. It should be clear that the function of the test coupon 20 is the same for configurations including one or more than four coupons.

An additional benefit of the introduction of the test coupons to the ballistic shield 30 is the resulting standoff spacing of the covering 15 from the shield 30 inside of each portion 10, 11. That is, the increase thickness of the test coupon over the shield 30 separates the covering 15 from the shield 30 in the areas surrounding the test coupon 20. This results in a gap between the covering 15 and the shield 30 over a substantial area of the portions 10, 11. If the covering 15 is formed of fabric that allows each airflow through the covering 15, air may circulate through this gap to enhance evaporation and cooling. For this reason, the test coupons 20 are preferably located on the outside surface of the shield 30, although they may also be located on the inside (closer to the user's body).

Preferably, the shield body 34, and hence test coupon body 24 are formed of a multilayer construction of substantially high-strength sheet materials. In many convention ballistic shield devices, materials formed of aramid fabrics or other forms of aramid materials. Aramids are generally materials generally prepared by the reaction between an amine group and a carboxylic acid halide group. These materials includes meta-aramids such as that sold under the trademark Kevlar by the United States company, E. I. du Pont de Nemours and Company. In the following, the term "aramid" refers to an element formed substantially by at least one form aramid material, or other material having like properties. The preferred construction of the shield body 34 (and hence the test coupon body 24) is a twenty-one layer assembly including: two outer (strike face) layers, each strike face layer including two sheets of woven aramid laminated together with a film layer between them (total weight/area density of 0.135 pounds per square foot). The film layer is substantially polyethylene. Behind the strike face are eighteen layers of unidirectional aramid material. This material is preferably a material supplied under the trademark Gold Flex by the Honeywell International Inc. company. Behind these is at least one layer of the same material as specified for the strike face. They are preferably not stitched together or otherwise interconnected. The assembled construction is secured within the shield cover 32 (or coupon cover 22). While the particular ballistic construction has been shown to be effective, other constructions are possible and may be incorporated in the invention without deviating from the invention.

Figure 5:
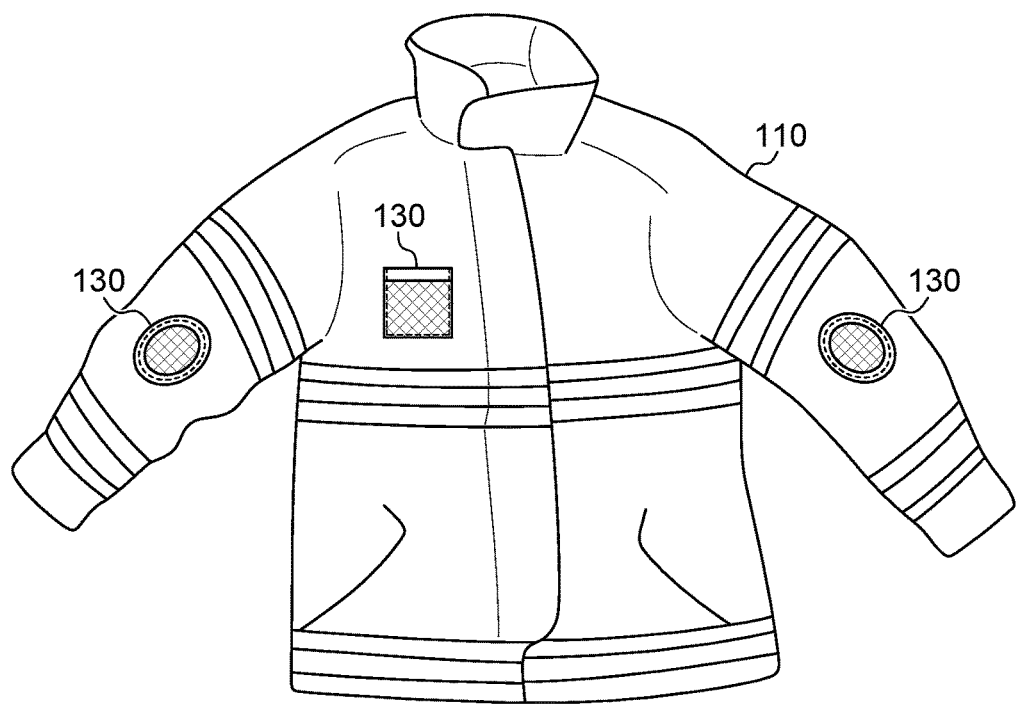
FIG. 5 is front view of another garment configuration according to the invention.
Figure 6:
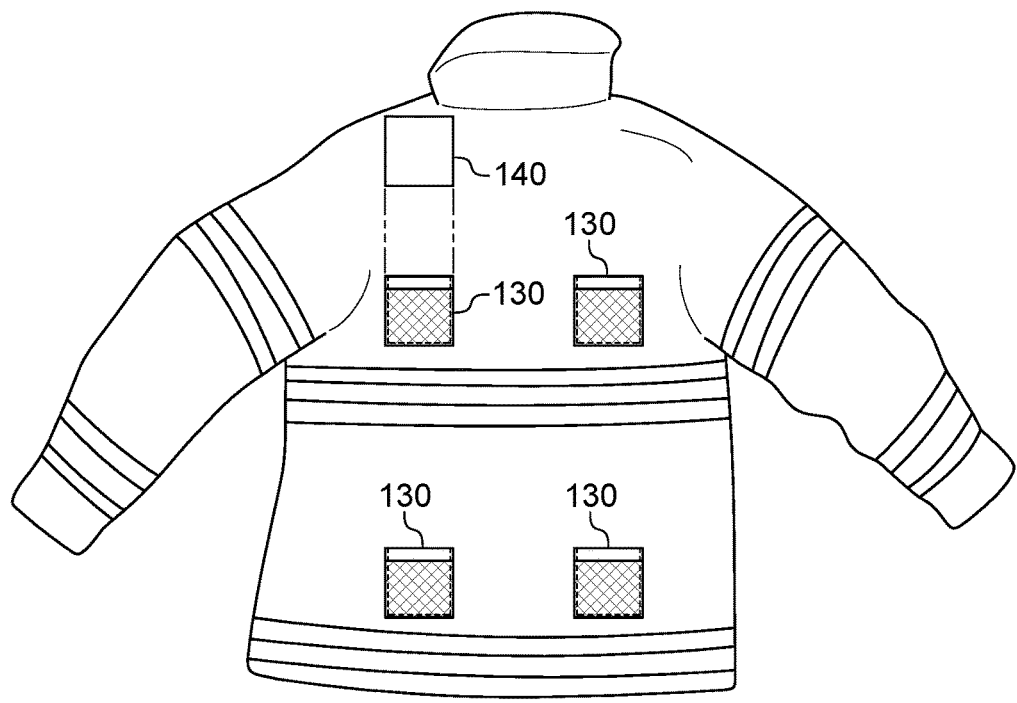
FIG. 6 is a back view of the garment of FIG. 5.

FIGS. 5, 6, 7A illustrate a common configuration of a garment with multiple test coupons for testing for acquired deleterious substances according to the invention. The garment in this example is a fire-fighter turnout gear jacket 110 that is designed to be wear on the torso of a person. For the purposes of performing as fire fighting turnout gear, the jacket 110 is formed of conventional known constructions and materials. However, for the purposes of the invention, the specifics of the construction and materials are not critical.

In all cases, the coupon 140 is formed of the same materials and construction as the garment 110, to provide a representative sample. Each coupon 140 is substantially smaller than the body of the garment and should be no larger than necessary to provide an effective test subject. This size may depend on the nature of the test of interest. In any case, the coupon 140 should have adequate size for handling and attachment and to avoid edge effects of adsorption and exposure and thus is generally planar (although possibly flexible) with a planar area substantially larger than the thickness.

At any or several of various different locations on the jacket 110, multiple test coupons 140 are individually retained on the outer surface of the jacket 110. The locations of the test coupons 140 are selected to provide to each test coupon 140 a representative exposure to the surrounding environment. For this reason, the locations may depend on the nature of an anticipated environmental substance or condition or other exposure factor and the nature of the mechanism by which the jacket 110 acquires the factor. For factors such as chemicals or toxic substances in the ambient air, it is believed that a particular location on the exterior surface is not critical.

Because it is necessary that each test coupon 140 be exposed generally to the same environment as the jacket 110, the test coupon 140 must be retained without entirely covering it or otherwise impeding the surrounding environmental air and other exposures from contacting and affecting the test coupon 140. This may be accomplished in any of a variety of ways.

In FIGS. 5 and 6, the test coupons 140 are shown enclosed in an outer fabric sleeve or pocket 130. A cross-section view of the pocket 130 and enclosed coupon 140 is illustrated in the cross-section view of FIG. 7A. To allow exposure of the coupon 140 within the pocket 130, the portions of the pocket 130 covering the coupon 140, or a test area of the coupon 140, must be open, in the nature of an substantially open mesh 135, or the equivalent, to allow free passage or communication of surrounding air into the pocket 130, or otherwise to contact the outer facing surface 141 of the coupon 140.

Preferably, the pocket 130 and coupon 140 are mutually configured to tightly fit together without intervening space between the coupon 140 and the surrounding air. Expressed in other terms, each coupon 140 should be biased outwardly against the pocket mesh 135 or opening so that there is no gap between the coupon 140 and the surrounding air. This configuration will be more effective in particular applications.

In various configurations, the coupons 140 may be partially covered with impervious or non-mesh material over a minor perimeter portion of a coupon 140 to effect a greater security, while a substantial portion of the coupons 140 are exposed as discussed above. In such a case, testing should be directed at the exposed portion.

Other methods and mechanisms for retaining the coupon 140, replacing the pocket 130 discussed above, include mechanical fasteners such as snaps, pins and conventional "hook and loop" fastening systems and temporary adhesives. FIG. 7B illustrates, in side view, a coupon 140 retained on a garment 110 by means of mating hook-and-loop fastener elements 150.

In methods according to the invention, it is beneficial to establish a desired useful life period for the garment as this will guide the testing periods. Knowledge of risk factors including potential substance exposure rates, rates of absorption, maximum limits for concentrations or content of substances on the subject garment can be the basis for determining the frequency and number of coupon testing needed. The garment construction with coupons, and the associated testing of coupons, can be effective for determining the presence of suspected substances. However, application of these constructions and methods to ensure limiting garment user exposures requires predetermination of the appropriate number of coupons and timing of testing.

Once an appropriate system of coupons and time periods for testing is determined, the garment may be entered into use with the associated coupons. Following the predetermined time periods, a different coupon is removed at the end of a use period and subjected to testing. Destructive testing may be used as it is inherent in the inventive methods that the coupons need not be returned to the garment. If the desired testing process requires multiple coupons at each testing time, sufficient coupons may be retained and removed as needed. If testing determines that the coupon (and hence the garment) does not exceed the concentration limits (or other detectable criteria) for the subject substance, the garment may continue to be used. Upon exceeding or determining the limit or criteria, the garment may be removed from service and use.

The above embodiments are provided as illustrative of the features and functions of the invention. One skilled in the art will understand or discover alternative configurations or constructions within the invention as defined by the claims.

The invention claimed is:

1. A method of enabling destruction testing of a garment, comprising:
 defining a useful garment life;
 providing a garment with a garment material construction;
 removably securing to the garment at least one test coupon comprising the garment material construction;
 during the useful life, removing one test coupon and performing destructive testing on the test coupon, and repeating with all test coupons.

2. A method of enabling destruction testing of a garment, according to claim 1, and wherein:
 the garment includes a ballistic shield.

3. A method of enabling destruction testing of a garment, according to claim 1, and wherein:
 the garment comprises firefighter turnout gear.

4. A method of enabling destructive testing of a garment, according to claim 1, and wherein:
 the step of removably securing to the garment at least one test coupon comprises retaining the at least one test coupon within a garment pocket.

\* \* \* \* \*